US006976966B2

(12) United States Patent
Narimatsu

(10) Patent No.: US 6,976,966 B2
(45) Date of Patent: Dec. 20, 2005

(54) ARTERIOSCLEROSIS EVALUATING APPARATUS

(75) Inventor: Kiyoyuki Narimatsu, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 44 days.

(21) Appl. No.: 10/724,086

(22) Filed: Dec. 1, 2003

(65) Prior Publication Data
US 2004/0122329 A1 Jun. 24, 2004

(30) Foreign Application Priority Data
Dec. 20, 2002 (JP) .............................. 2002-369972

(51) Int. Cl.$^7$ ................................................ A61B 5/02
(52) U.S. Cl. ...................... 600/494; 600/490; 600/495; 600/500
(58) Field of Search ............................... 600/481, 485, 600/490, 491–496, 500–503

(56) References Cited

U.S. PATENT DOCUMENTS

| | | | | |
|---|---|---|---|---|
| 4,880,013 A | * | 11/1989 | Chio | 600/494 |
| 5,000,188 A | | 3/1991 | Kojima | |
| 5,680,867 A | * | 10/1997 | Shimazu et al. | 600/490 |
| 5,913,826 A | * | 6/1999 | Blank | 600/500 |
| 5,961,467 A | * | 10/1999 | Shimazu et al. | 600/485 |
| 6,315,734 B1 | | 11/2001 | Nunome | |
| 6,491,638 B2 | | 12/2002 | Oka | |
| 6,612,993 B2 | * | 9/2003 | Narimatsu | 600/500 |
| 2003/0040675 A1 | * | 2/2003 | Sharrock | 600/490 |

FOREIGN PATENT DOCUMENTS

| | | |
|---|---|---|
| JP | A-2000-139859 | 5/2000 |
| JP | A 2001-346769 | 12/2001 |

OTHER PUBLICATIONS

Yoshiaki Masuda, Hiroshi Kanai "Fundamental and Clinical Study of Arterial Pulse Wave," 1$^{st}$ Edition, pp. 28-31, Kyoritsu Shuppan K.K., Mar. 2000.
Joseph P. Murgo, M.D . et al. vol. 62; No. 1; pp. 105-116; Jul. 1980 Circulation "Aortic Input Impedance in Normal Man: Relationship to Pressure Wave Forms." Mar. 31, 2000.

* cited by examiner

Primary Examiner—Robert L. Nasser
Assistant Examiner—Navin Natnithithadha
(74) Attorney, Agent, or Firm—Oliff & Berridge, PLC

(57) ABSTRACT

An arteriosclerosis evaluating apparatus for evaluating an arteriosclerosis of a living subject based on a form of a pulse wave detected from the subject, the apparatus including an inflatable cuff which is adapted to be worn on a body portion of the subject, a cuff-pressure changing device which changes a pressure in the cuff, a cuff-pulse-wave detecting device which detects a cuff pulse wave as a pressure oscillation that is transmitted from the subject to the cuff, and an output device which outputs the cuff pulse wave detected by the cuff-pulse-wave detecting device in a state in which the pressure of the cuff is made higher than a systolic blood pressure of the body portion of the subject by the cuff-pressure changing device.

4 Claims, 4 Drawing Sheets

TYPE I

TYPE II

TYPE III

TYPE IV

TIME

ARTERIOSCLEROSIS EVALUATING APPARATUS

BACKGROUND OF THE INVENTION

1. Field of the Invention

The present invention relates to an arteriosclerosis evaluating apparatus that evaluates a degree of arteriosclerosis of a living being, based on a form of a cuff pulse wave obtained from the being.

2. Related Art Statement

It is known that the form of a pulse wave produced from an artery changes as the artery hardens. Hence, there is known a method of evaluating a degree of arteriosclerosis of a patient by judging which one of predetermined types of waveform patterns corresponding to different degrees of arteriosclerosis the form of an arterial pulse wave detected from the patient is classified as. For example, there is known a method of classifying a detected pulse wave as one of four types, based on a percussion wave and a tidal wave of the pulse wave (e.g., cf. Non-Patent Document 1 (Yoshiaki Masuda, Hiroshi Kanai "Fundamental and Clinical Study of Arterial Pulse Wave", $1^{st}$ Edition, p.28–31, Kyoritsu Shuppan K. K., March 2000)). The four types include Type I characterized in that the percussion wave is higher than the tidal wave; Type II characterized in the tidal wave is higher than the percussion wave and a clear local minimum point is present between the two waves; Type III characterized in that the two waves are incompletely fused with each other; and Type IV characterized in that the two waves are completely fused with each other. Type I is the lowest degree of arteriosclerosis, the possibility of advancement of arteriosclerosis increases as the number increases, and Type IV is the evaluation of the highest degree of arteriosclerosis. FIG. 2 shows respective typical waveform patterns corresponding to Types I, II, III, and IV. In FIG. 2, p-wave indicates a percussion wave; and t-wave indicates a tidal wave.

There is also known a method of classifying a pulse wave as one of three types, based on respective peaks of a percussion wave and a tidal wave of the pulse wave (e.g., cf. Non-Patent Document 2 (Joseph P. Murgo, Nico Westerhof, John P. Giolma, Stephen A. Altobelli, "Aortic Input Impedance in Normal Man: Relationship to Pressure Wave Forms", Circulation, Vol. 62, No. 1, p105–116, July 1980)). The three types include Type A characterized in that the peak of the percussion wave is higher than that of the tidal wave; Type B characterized in the respective peaks of the percussion wave and the tidal wave are level with each other; and Type C characterized in that the peak of the tidal wave is higher than that of the percussion wave.

Meanwhile, blood-pressure measuring devices each employing a cuff are widely used. Hence, there have been proposed various devices that obtain, from a cuff pulse wave detected from the cuff, other sorts of physical information than blood pressure. For example, Patent Document 1 (i.e., Japanese Patent Document No. 2001-346769 or its corresponding U.S. Pat. No. 6,491,638) discloses a device that determines a pulse period, i.e., a pulse rate from a time interval between respective periodic points, such as rising points or peak points, of successive heartbeat-synchronous pulses of a cuff pulse wave. The cuff pulse wave is detected from a cuff in a state in which a pressure in the cuff is lower than a diastolic blood pressure of a living subject, because it has been speculated that if the pressure of the cuff is higher than the diastolic blood pressure, then the cuff pulse wave detected is distorted and accordingly does not have an accurate form.

In the above-described method in which arteriosclerosis is evaluated based on the form of a pulse wave, a cuff pulse wave may be used as it is used in the device disclosed by Patent Document 1. However, it has been elucidated that a cuff pulse wave detected in the state in which the pressure of a cuff is lower than a diastolic blood pressure of a living subject, has a problem that a high-frequency component of the cuff pulse wave is not clear. Since the high-frequency component of the cuff pulse wave includes the above-mentioned percussion and tidal waves, i.e., those portions that change as the degree of arteriosclerosis changes, a degree of arteriosclerosis evaluated based on the form of the cuff pulse wave detected in the state in which the pressure of the cuff is lower than the diastolic blood pressure of the subject, cannot enjoy a sufficiently high accuracy.

SUMMARY OF THE INVENTION

It is therefore an object of the present invention to provide an arteriosclerosis evaluating apparatus that can accurately evaluate a degree of arteriosclerosis of a living being, based on a form of a cuff pulse wave.

The Inventor has carried out extensive studies to achieve the above-indicated object, and found that a low-frequency component of a cuff pulse wave detected from a cuff in a state in which a pressing pressure in the cuff is not lower than a systolic blood pressure of a body portion on which the cuff is worn, is distorted due to the high pressing pressure, but a high-frequency component of the cuff pulse wave is clearer than that of a cuff pulse wave detected in a state in which the pressing pressure of the cuff is lower than a diastolic blood pressure of the body portion. The present invention has been developed based on this finding.

The above object has been achieved by the present invention. According to a first aspect of the present invention, there is provided an arteriosclerosis evaluating apparatus for evaluating an arteriosclerosis of a living subject based on a form of a pulse wave detected from the subject, the apparatus comprising an inflatable cuff which is adapted to be worn on a body portion of the subject; a cuff-pressure changing device which changes a pressure in the cuff, a cuff-pulse-wave detecting device which detects a cuff pulse wave as a pressure oscillation that is transmitted from the subject to the cuff, and an output device which outputs the cuff pulse wave detected by the cuff-pulse-wave detecting device in a state in which the pressure of the cuff is made higher than a systolic blood pressure of said body portion of the subject by the cuff-pressure changing device.

According to the first aspect of the present invention, the output device outputs a waveform of the cuff pulse wave detected in the state in which the pressing pressure of the cuff is higher than the systolic blood pressure of the body portion of the subject. The high-frequency component of the thus detected cuff pulse wave is accurate. Therefore, if a person such as a doctor judges, based on the high-frequency component of the cuff pulse wave outputted by the output device, which type of pattern the waveform of the cuff pulse wave is classified as, then the person can accurately evaluate a degree of arteriosclerosis of the subject.

According to a second aspect of the present invention, there is provided an arteriosclerosis evaluating apparatus, comprising an inflatable cuff which is adapted to be worn on a body portion of a living subject; a cuff-pressure changing device which changes a pressure in the cuff a cuff-pulse-wave detecting device which detects a cuff pulse wave as a pressure oscillation that is transmitted from the subject to the cuff, and a waveform-pattern determining means for determining a waveform pattern corresponding to a form of a high-frequency component of the cuff pulse wave detected by the cuff-pulse-wave detecting device in a state in which the pressure of the cuff is made higher than a systolic blood pressure of the body portion of the subject by the cuff-pressure changing device, according to a predetermined relationship between form of high-frequency component of pulse wave, and waveform pattern corresponding to degree of arteriosclerosis.

According to the second aspect of the present invention, the waveform-pattern determining means determines the waveform pattern corresponding to the form of the high-frequency component of the cuff pulse wave, and the cuff pulse wave is detected in the state in which the pressing pressure of the cuff is higher than the systolic blood pressure of the body portion of the subject. Therefore, the waveform-pattern determining means determines, based on the cuff pulse wave whose high-frequency component is accurate, the waveform pattern corresponding to the degree of arteriosclerosis of the subject. Thus, the present arteriosclerosis evaluating apparatus can accurately evaluate the degree of arteriosclerosis of the subject.

Here, preferably, the predetermined relationship comprises a predetermined relationship between respective forms of percussion and tidal waves as high-frequency component of pulse wave, and waveform pattern. This relationship is disclosed by, e.g., Non-Patent Document 1 or Non-Patent Document 2.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
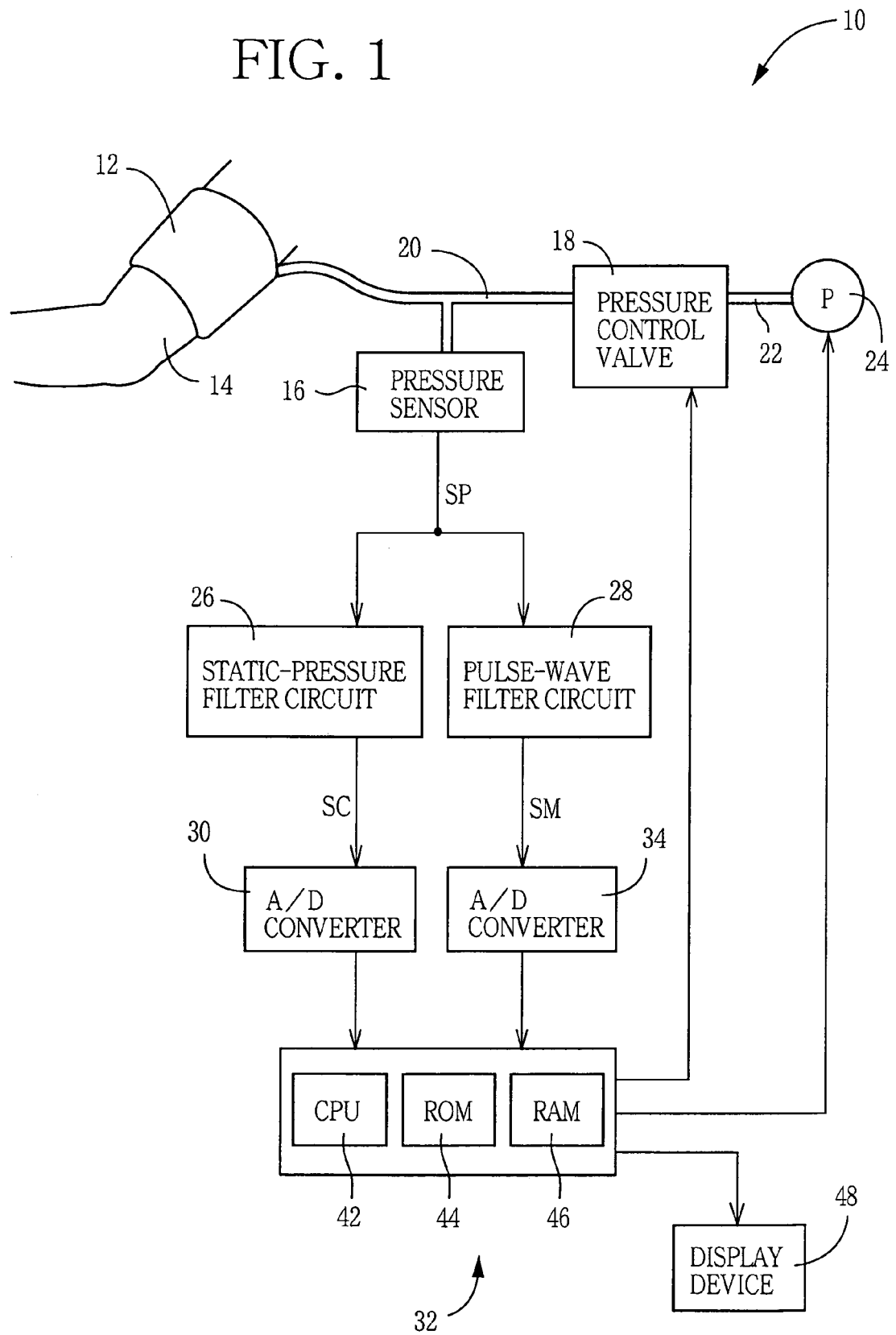
FIG. 1 is a diagrammatic view for explaining a circuitry of an arteriosclerosis evaluating apparatus to which the present invention is applied.

Hereinafter, there will be described an embodiment of the present invention in detail by reference to the drawings. FIG. 1 is a diagrammatic view for explaining a circuitry of an arteriosclerosis evaluating apparatus 10 to which the present invention is applied.

In FIG. 1, the arteriosclerosis evaluating apparatus 10 includes a cuff 12 that includes a belt-like cloth bag and an inflatable rubber bag accommodated in the cloth bag, and that is wrapped around a brachial portion 14 of a patient as a living subject. The cuff 12 is connected via a pipe 20 to a pressure sensor 16 and a pressure control valve 18, and the pressure control valve 18 is connected via a pipe 22 to an air pump 24. The pressure control valve 18 adjusts a pressure of a pressurized air supplied from the air pump 24, and supplies the pressure-adjusted air to the cuff 12, or discharges the air from the cuff 12, so as to control the air pressure in the cuff 12.

The pressure sensor 24 detects the air pressure in the cuff 20, and supplies a pressure signal SP representing the detected air pressure, to each of a static-pressure filter circuit 26 and a pulse-wave filter circuit 28. The static-pressure filter circuit 26 includes a low-pass filter that extracts, from the pressure signal SP, a cuff-pressure signal SC representing a static component of the detected air pressure, i.e., a pressing pressure of the cuff 12 (hereinafter, referred to as the cuff pressure PC). The filter circuit 26 supplies the cuff-pressure signal SC to an electronic control device 32 via an A/D (analog-to-digital) converter 30. The pulse-wave filter circuit 28 includes a band-pass filter that allows passing therethrough of a signal having frequencies in a range of, e.g., from 1 to 30 Hz and that extracts, from the pressure signal SP, a cuff-pulse-wave signal SM representing an oscillatory component of the detected air pressure. The filter circuit 28 supplies the cuff-pulse-wave signal SM to the electronic control device 32 via an A/D converter 34. The cuff-pulse-wave signal SM represents a cuff pulse wave as a pressure oscillation that is transmitted from an artery of the subject to the cuff 12. Thus, the pulse-wave filter circuit 28 functions as a cuff-pulse-wave detecting device. Since the artery is a brachial artery, the cuff pulse wave provides a brachial pulse wave.

The electronic control device 32 is provided by a so-called microcomputer including a CPU (central processing unit) 42, a ROM (read only memory) 44, a RAM (random access memory) 46, and an I/O (input-and-output) port, not shown. The CPU 42 processes signals according to the control programs pre-stored in the ROM 44 by utilizing the temporary-storage function of the RAM 46, and supplies drive signals via the I/O port to the air pump 24 and the pressure control valve 18, so as to control the cuff pressure PC. In addition, the CPU 42 has various functions, illustrated in detail in FIG. 3, that are for determining a waveform pattern corresponding to a cuff pulse wave, and operates a display device 48 functioning as an output device, so that the display device 48 displays the determined waveform pattern together with the cuff pulse wave.

Figure 3:
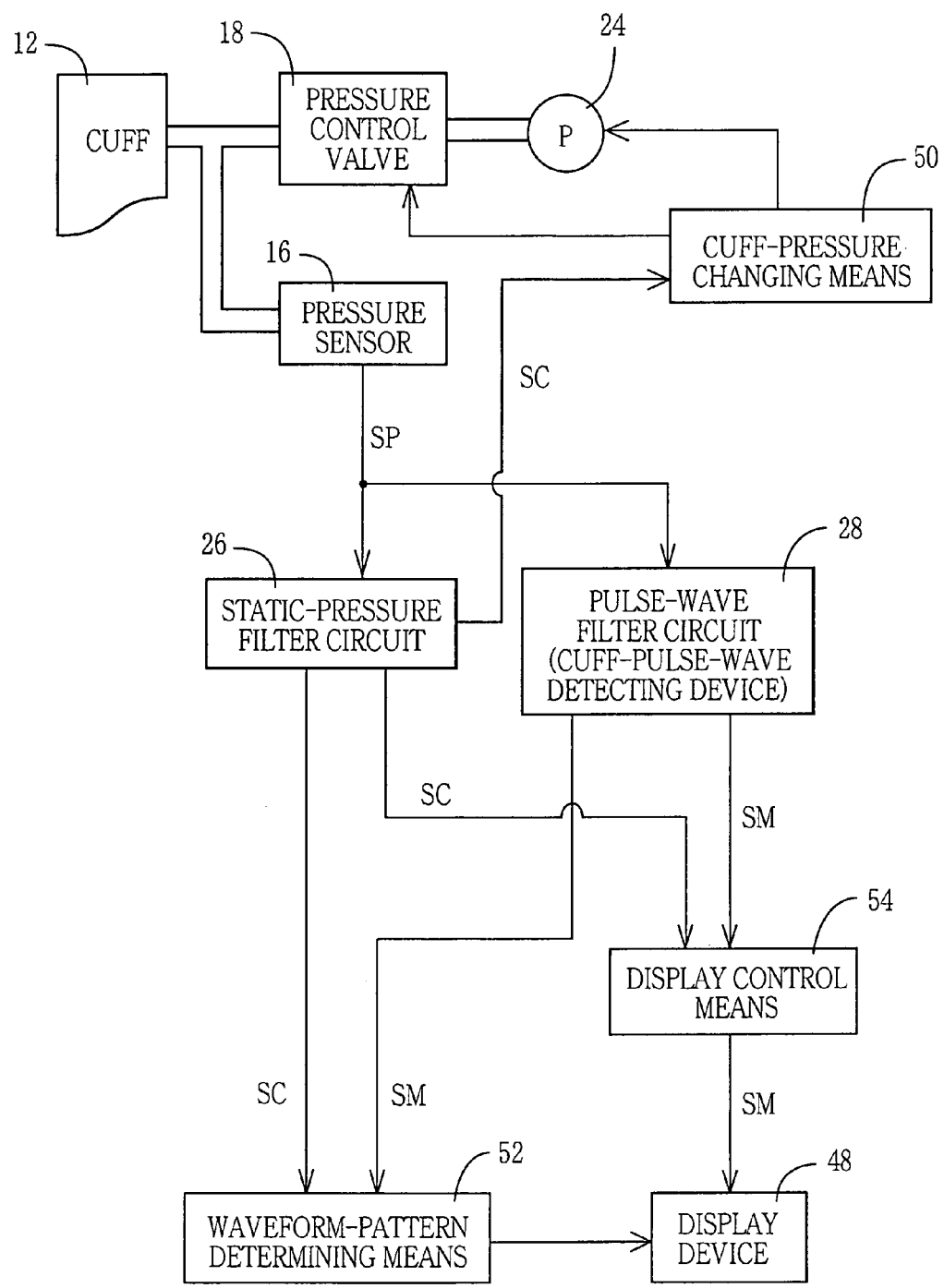
FIG. 3 is a diagrammatic view for explaining essential control functions of an electronic control device of the arteriosclerosis evaluating apparatus shown in FIG. 1.

FIG. 3 is a diagrammatic view for explaining essential control functions of the electronic control device 32 of the arteriosclerosis evaluating apparatus 10.

A cuff-pressure changing means 50 determines the cuff pressure PC based on the cuff-pressure signal SC supplied from the static-pressure filter circuit 26, and operates the pressure control valve 18 and the air pump 24, so as to change the cuff pressure PC to a pre-set artery-occlusion pressure PCa (e.g., 180 mmHg) that would be higher than a systolic blood pressure of the brachial portion 14. In the present embodiment, the static-pressure filter circuit 26, the pressure control valve 18, the air pump 24, and the cuff-pressure changing means 50 cooperate with each other to provide a cuff-pressure changing device.

A waveform-pattern determining device or means 52 determines, according to a waveform-pattern determination relationship pre-stored in the ROM 44, a waveform pattern corresponding to the cuff-pulse-wave signal SM (i.e., the cuff pulse wave) supplied from the pulse-wave filter circuit 28 when the cuff pressure PC is made equal to the artery occlusion pressure PCa by the cuff-pressure changing means 50, and operates the display device 48 to display the waveform pattern determined. The waveform-pattern determination relationship is a relationship between cuff pulse waves, and waveform patterns corresponding to degrees of arteriosclerosis. In the present embodiment, the relationship disclosed by the above-indicated Non-Patent Document 1 is used. That is, the relationship is for classifying each pulse wave as an appropriate one of the four types I, II, III, IV, based on percussion and tidal waves of the each pulse wave as the high-frequency component thereof. When the waveform pattern determined is displayed by the display device 48, a person such as a doctor can know subject's degree of arteriosclerosis from the waveform pattern displayed.

A display control device or means 54 operates the display device 48 to display the pulse wave for which the waveform pattern has been determined by the waveform-pattern determining means 52, that is, one of successive heartbeat-synchronous pulses that has been extracted (or detected) by the pulse-wave filter circuit 28 when the cuff pressure PC is made equal to the artery-occlusion pressure PCa by the cuff-pressure changing means 50.

Figure 2:
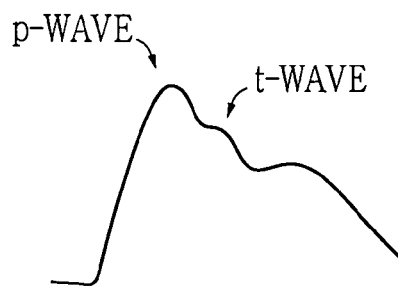
FIG. 2 is a graph showing respective typical waveform patterns of four known types I, II, III, and IV corresponding to four degrees of arteriosclerosis.
Figure 2:
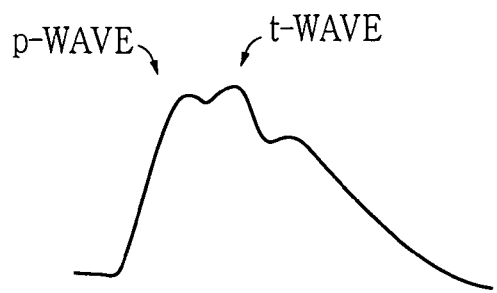
Figure 2:
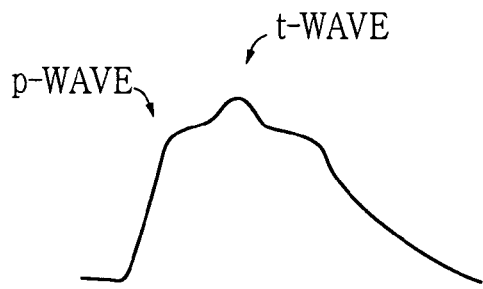
Figure 2:
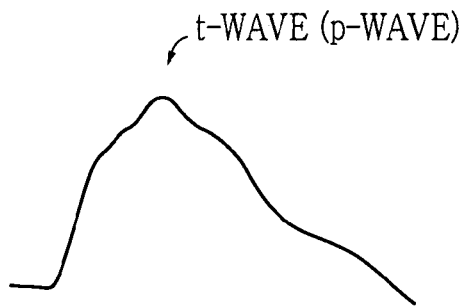
Figure 4:
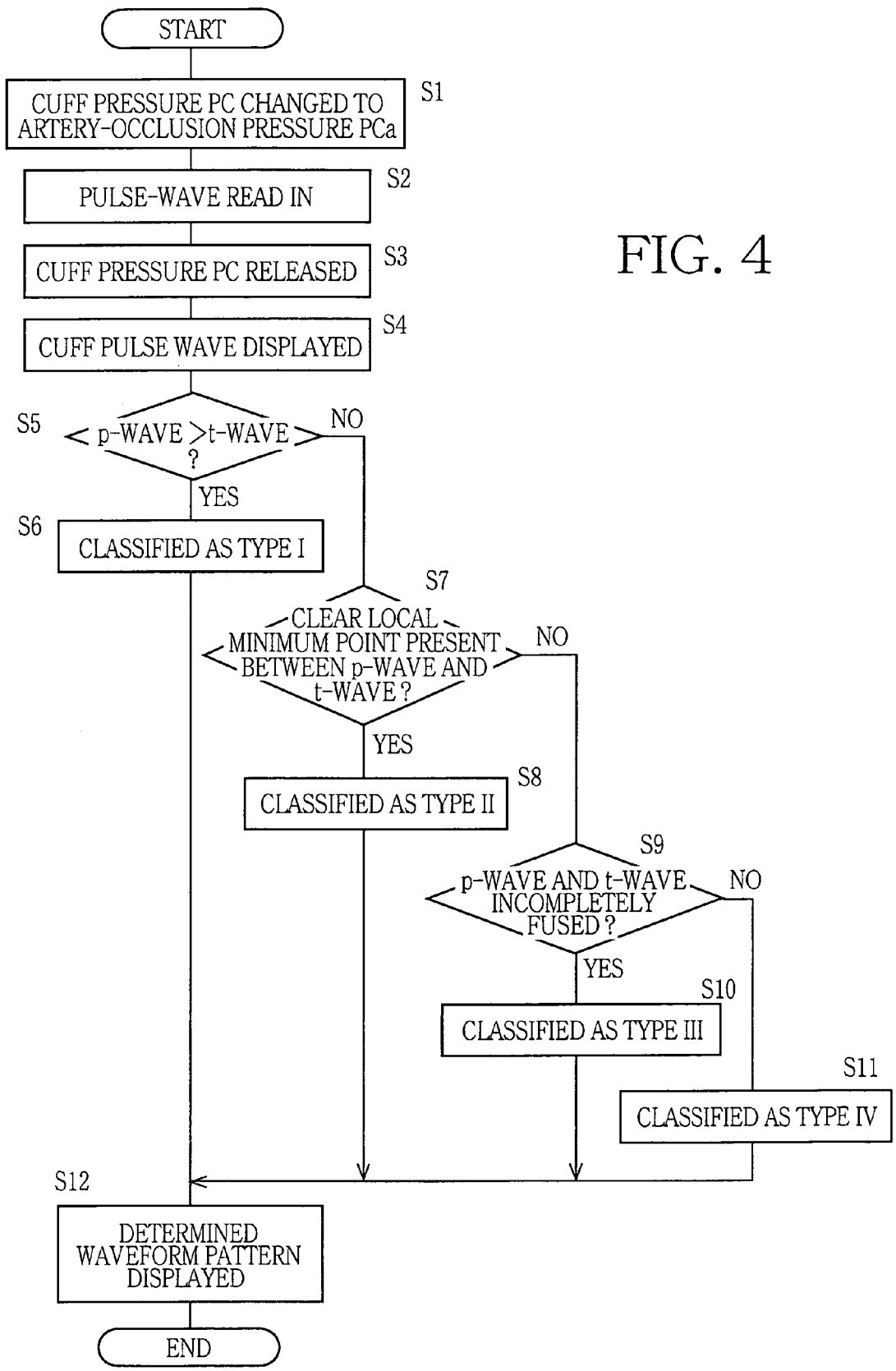
FIG. 4 is a flow chart for explaining a control routine according to which a waveform-pattern determining means, shown in FIG. 3, determines a waveform pattern corresponding to a cuff pulse wave obtained from a living subject.

FIG. 4 is a flow chart for explaining the essential control functions of the CPU 42, shown in the diagrammatic view of FIG. 2.

In FIG. 4, first, the CPU carries out Step S1 (hereinafter, "Step" is omitted) where the CPU starts the air pump 24 and operates the pressure control valve 18 to change the cuff pressure PC to the artery-occlusion pressure PCa pre-set at, e.g., 180 mmHg.

Subsequently, at S2, the CPU reads in one heartbeat-synchronous pulse of the cuff pulse wave represented by the cuff-pulse-wave signal SM supplied from the pulse-wave filter circuit 28 in a state in which the cuff pressure PC is kept at the artery-occlusion pressure PCa. S2 is followed by S3 to release the cuff pressure PC down to an atmospheric pressure. In the flow chart of FIG. 4, S1 and S3 correspond to the cuff-pressure changing means 50. Then, the control goes to S4 corresponding to the display control means 54. At S4, the control device operates the display device 48 to display a waveform of the one heartbeat-synchronous pulse of the cuff pulse wave, read in at S2.

Subsequently, the control goes to S5 through S12 corresponding to the waveform-pattern determining means 52. First, at S5, the CPU judges whether a magnitude of a percussion wave, i.e., p-wave of the one pulse of the cuff pulse wave is greater than a magnitude of a tidal wave, i.e., t-wave of the same pulse. If a positive judgment is made at S5, the control goes to S6 to classify the cuff pulse wave as Type I. On the other hand, if a negative judgment is made at S5, the control goes to S7 to judge whether a clear local minimum point is present between the p-wave and the t-wave. If a positive judgment is made at S7, the control goes to S8 to classify the cuff pulse wave as Type II.

On the other hand, if a negative judgment is made at S7, the control goes to S9 to judge whether the fusion of the p-wave and the t-wave is incomplete. If a positive judgment is made at S9, the control goes to S10 to classify the cuff pulse wave as Type III. On the other hand, if a negative judgment is made at S9, the fusion of the p-wave and the t-wave is complete and accordingly the control goes to S11 to classify the cuff pulse wave as Type IV. Then, the control goes to S12 to operates the display device 48 to display the waveform pattern of the type determined at S6, S8, S10, or S11.

In the illustrated embodiment, the CPU operates, at S4, the display device 48 to display the waveform of the cuff pulse wave detected in the state in which the cuff pressure PC is higher than the systolic blood pressure of the brachial portion 14 of the subject. The high-frequency component of the thus detected cuff pulse wave is accurate. Therefore, if a person such as a doctor judges, based on the high-frequency component of the cuff pulse wave displayed by the display device 48, as which type of pattern the waveform of the cuff pulse wave is classified, then the person can accurately evaluate the degree of arteriosclerosis of the subject.

In the illustrated embodiment, the display device 48 displays not only the waveform of the detected cuff pulse wave so that the person can judges as which type of waveform pattern the cuff pulse wave is classified, but also the waveform pattern automatically determined by the waveform-pattern determining means 52 (S5 through S12). The waveform-pattern determining means 52 (S5 through S12) determines the waveform pattern of the cuff pulse wave based on the form of the high-frequency component of the pulse wave, and the pulse wave is detected in the state in which the cuff pressure PC is higher than the systolic blood pressure of the brachial portion 14 of the subject. Therefore, the determining means 52 determines, based on the pulse wave whose high-frequency component is accurate, the waveform pattern of the pulse wave that corresponds to the degree of arteriosclerosis of the subject. Thus, the arteriosclerosis evaluating apparatus 10 can accurately evaluate the degree of arteriosclerosis of the subject.

While the present invention has been described in its embodiment by reference to the drawings, it is to be understood that the invention may otherwise be embodied.

For example, the cuff 12 may be used for measuring a blood pressure of the subject. In this case, the artery-occlusion pressure PCa may be determined based on a systolic blood pressure of the brachial portion 14 that is measured using the cuff 12.

In addition, in the illustrated embodiment, the cuff 12 is adapted to be worn on the brachial portion 14 of the subject. However, the cuff 12 may be adapted to be worn on a different portion of the subject, such as a femoral portion or an ankle.

In addition, in the illustrated embodiment, the display device 48 is employed as the output device. However, in place of, or in addition to, the display device 48, it is possible to employ a printer as the output device.

While the present invention has been described in its embodiments in detail by reference to the drawings, it may be understood that the present invention is by no means limited to the details of the embodiments but may be embodied with various changes and improvements that may occur to a person skilled in the art.

What is claimed is:

1. An arteriosclerosis evaluating apparatus, comprising:
an inflatable cuff which is adapted to be worn on a body portion of a living subject;
a cuff-pressure changing device which changes a pressure in the cuff;
a cuff-pulse-wave detecting device which detects a cuff pulse wave as a pressure oscillation that is transmitted from the subject to the cuff; and
a waveform-pattern determining means for determining a waveform pattern corresponding to a form of a high-frequency component of the cuff pulse wave detected by the cuff-pulse-wave detecting device in a state in which the pressure of the cuff is made higher than a systolic blood pressure of said body portion of the subject by the cuff-pressure changing device, according to a predetermined relationship between form of high-frequency component of pulse wave, and waveform pattern corresponding to degree of arteriosclerosis;
wherein the predetermined relationship comprises a predetermined relationship between respective forms of percussion and tidal waves of pulse wave, and the waveform pattern corresponding to degree of arteriosclerosis.

2. An arteriosclerosis evaluating apparatus according to claim 1, further comprising a memory which stores the predetermined relationship.

3. An arteriosclerosis evaluating apparatus according to claim 1, further comprising an output device which outputs at least one of (a) the cuff pulse wave detected by the cuff-pulse-wave detecting device in the state in which the pressure of the cuff is made higher than the systolic blood pressure of said body portion of the subject by the cuff-pressure changing device and (b) the waveform pattern determined by the waveform-pattern determining means.

4. An arteriosclerosis evaluating apparatus according to claim 3, wherein the output device outputs each of (a) the cuff pulse wave detected by the cuff-pulse-wave detecting device in the state in which the pressure of the cuff is made higher than the systolic blood pressure of said body portion of the subject by the cuff-pressure changing device and (b) the waveform pattern determined by the waveform-pattern determining means.

* * * * *